United States Patent [19]

Bertholet

[11] Patent Number: 4,692,534

[45] Date of Patent: Sep. 8, 1987

[54] PREPARATION OF CAFESTOL

[75] Inventor: Raymond Bertholet, Blonay, Switzerland

[73] Assignee: Nestec S.A., Vevey, Switzerland

[21] Appl. No.: 847,488

[22] Filed: Apr. 3, 1986

[51] Int. Cl.⁴ .......................................... C07D 307/77
[52] U.S. Cl. .................................................... 549/456
[58] Field of Search ........................................ 549/456

[56] References Cited
PUBLICATIONS

Djerassi et al., J. Org. Chem., vol. 18, pp. 1449–1460, (1953).

*Primary Examiner*—Richard A. Schwartz
*Assistant Examiner*—Bernard I. Dentz
*Attorney, Agent, or Firm*—Vogt & O'Donnell

[57] ABSTRACT

A process for the preparation of cafestol from kahweol wherein the kahweol is hydrogenated in the presence of a partially deactivated palladium catalyst on a calcium carbonate or active carbon support conditioned by lead. A process for preparing a mixture of cafestol and kahweol by treating coffee oil with anhydrous methanol in the presence of a basic catalyst is also disclosed.

18 Claims, No Drawings

PREPARATION OF CAFESTOL

The present invention relates to the preparation of cafestol from kahweol and more especially to the preparation of substantially pure cafestol from a crude mixture of kahweol and cafestol derived from coffee oil.

Coffee oil comprises significant amounts of the esters of two furanic diterpenes: cafestol and kahweol. The actual amounts present vary according to the origin of the coffee. For example, there is no kahweol present in Robusta coffee while Arabica contains a mixture of kahweol and cafestol in the approximate ratio of 1:3. The average composition of coffee oil is as follows:

| Triglycerides | 75–80% |
|---|---|
| Esters of cafestol and kahweol | 7–15% |
| Steroids | 2–3% |
| Phosphatides | 1–5% |

The formulae of cafestol and kahweol are indicated by the following formulae I and II respectively:

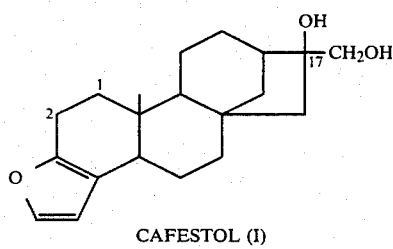

CAFESTOL (I)

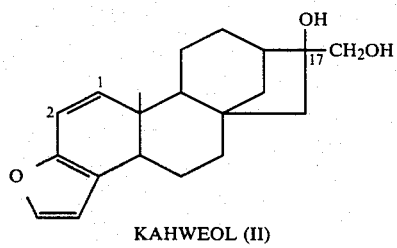

KAHWEOL (II)

It can readily be seen that the only difference between the two compounds is the presence of a double bond between positions 1 and 2 in kahweol. The esters of the cafestol and kahweol present in coffee oil are mainly the palmitates and the lineoleates in position 17.

Clearly, in order to prepare substantially pure cafestol, it is first necessary to liberate the free diterpenes, cafestol and kahweol, from the coffee oil by means of a hydrolysis step and then to convert the kahweol in the mixture of diterpenes into cafestol by hydrogenation of the double bond between positions 1 and 2 but not the double bonds of the furan nucleus.

In previous work, pure cafestol has been obtained from a mixture of kahweol and cafestol by a known hydrogenation method using a sodium-ethanol mixture to give nascent hydrogen. However, although kahweol can be reduced to cafestol by this method there are two major disadvantages:

(1) three to four successive hydrogenations are necessary;

(2) the dissolution of metallic sodium in ethanol is an extremely delicate manipulation.

Other processes are known which employ hydrogen and a catalyst, e.g., palladium on active carbon or on barium sulphate. However, in these processes, hydrogenation of all the double bonds of the kahweol occurs so that it is reduced to tetrahydrocafesol which is then separated from the cafestol by crystallisation. Therefore, the kahweol is not converted to cafestol and the yield is accordingly not as high as is desired.

We have now found, surprisingly, that by using a partially deactivated palladium catalyst on a calcium carbonate or active carbon support conditioned by lead, the kahweol is converted almost completely into cafestol the double bonds of the furan nucleus not being affected.

Accordingly, the present invention provides a process for the preparation of cafestol from kahweol characterised in that the kahweol is hydrogenated in the presence of a partially deactivated palladium catalyst on a calcium carbonate or active carbon support conditioned by lead.

The conditioning is carried out to partially deactivate, or to moderate the activity of the palladium by electrochemical exchange with the lead and may conveniently be effected by heating with an aqueous solution of lead acetate in water followed by filtering, washing and drying. Preferably, the heating is carried out with agitation, for instance, at a temperature from 60° C. to 95° C. and for a period of time conveniently from 30 to 60 minutes. Such catalysts are commonly used for reducing triple to double bonds and an example of the preparation of a suitable catalyst is described in Organic Synthesis, Vol. 5, Baumgartner pp 880–883.

Palladium is generally sold commercially on four different inert supports:
  calcium carbonate
  active carbon
  barium sulphate
  aluminium oxide These catalysts may be conditioned with lead but we have found that kahweol is converted into cafestol in good yields only when the support used is calcium carbonate or active carbon. When the support used is barium sulphate the kahweol is destroyed and when the support used is aluminium oxide, only a minor proportion of the kahweol is converted to cafestol.

The amount of catalyst used is conveniently from 0.1 to 1.0, preferably from 0.25 to 0.75 and especially from 0.4 to 0.6 parts by weight per part by weight of kahweol.

The hydrogenation reaction preferably takes place in a suitable solvent such as an aliphatic alcohol or an aromatic hydrocarbon. The aliphatic alcohol advantageously contains from 1 to 3 carbon atoms and may be, for instance ethanol. The aromatic hydrocarbon is preferably benzene or toluene. The amount of solvent is suitably from 10 to 100 parts and preferably from 20 to 50 parts by weight per part by weight of the kahweol.

The duration of the hydrogenation is not critical and is conveniently from 0.5 to 5 hours, preferably from 1 to 3 hours. Ambient temperatures and atmospheric pressure are suitable for the process.

After hydrogenation, the reaction solution may be separated from the catalyst, for instance by filtration, and the cafestol may be precipitated by the addition of water to the concentrated filtrate and afterwards, if desired, recrystallised in a suitable solvent such as a lower aliphatic alcohol, ester, ketone, ether or an aromatic hydrocarbon. Examples of suitable solvents are $C_1$–$C_4$ alcohols, $C_1$–$C_4$ alkyl esters of formic or acetic acid, ketones containing from 3 to 5 carbon atoms, diethylether, diisopropylether, benzene or toluene.

The process of this invention is particularly applicable for the preparation of substantially pure cafestol from a mixture comprising cafestol and kahweol, especially a crude mixture of cafestol and kahweol derived from coffee oil. Such crude mixtures derived from coffee oil may contain between about 15 and 50% kahweol and more usually from 20 to 45% kahweol. These mixtures may be obtained by hydrolysis of the coffee oil followed by the selective extraction of cafestol and kahweol e.g., saponification followed by extraction of the unsaponifiables by a solvent such as methylene dichloride. However, such methods require extremely large volumes of solvent and heating at about 80° C. for a prolonged period which can cause the decomposition of the kahweol owing to its heat-sensitivity.

We have developed an improved method of obtaining a mixture of cafestol and kahweol from coffee oil which involves a transesterification process using anhydrous methanol in the presence of a basic catalyst followed by extraction. The use of the methanol enables the process to be carried out at ambient temperature, thus avoiding any thermal decomposition of the kahweol.

Accordingly, the present invention also provides a process for preparing a mixture of cafestol and kahweol characterised in that coffee oil is treated with anhydrous methanol in the presence of a basic catalyst, the reaction medium is diluted with a substantially water-insoluble solvent which dissolves the formed methyl esters and then is extracted with aqueous methanol, the aqueous methanol phase then being separated and further extracted with a low-boiling chlorinated hydrocarbon which is then separated from the aqueous methanol phase and evaporated to give the mixture of cafestol and kahweol.

The treatment of the coffee oil with the anhydrous methanol is preferably carried out at ambient temperature with agitation for a minimum of 1 hour, preferably from 2 to 6 hours. The amount of methanol used is conveniently from 20% to 100%, preferably from 30% to 80% and especially from 40% to 60% by weight based on the weight of coffee oil.

The basic catalyst is suitably sodium hydroxide, potassium hydroxide or potassium carbonate and the amount used may be from 0.1 to 10%, preferably from 0.5 to 5% and especially from 1% to 4% by weight based on the weight of coffee oil.

In the treatment of the coffee oil with anhydrous methanol in the presence of a basic catalyst, the triglycerides and the esters are converted into the fatty acid methyl esters and alcohols (glycerol, sterols, cafestol and kahweol). The substantially water-insoluble solvent which dissolves the fatty acid methyl esters should be liquid under the conditions of the reaction and may be a $C_5$–$C_{14}$ alkane, for example, heptane. The amount of solvent is conveniently from 0.5 to 3 parts and preferably from 1 to 2 parts by weight based on the weight of coffee oil.

The aqueous methanol preferably contains from about 2% to 15% and preferably from 4% to 12% by weight of water based on the weight of methanol. The aqueous methanol phase contains the cafestol, kahweol, glycerol and the basic catalyst in solution. When the aqueous methanol phase has been separated, it is then extracted with the low-boiling chlorinated hydrocarbon to permit the cafestol and kahweol to be isolated.

The low-boiling chlorinated hydrocarbon is preferably dichloromethane.

Kahweol possesses an interesting ultra-violet absorption spectra and the mixture of cafestol and kahweol can be used in cosmetic applications either in the crude form obtained as above or after recrystallisation. Cafestol has antiinflammatory properties.

The following Examples further illustrate the present invention.

EXAMPLE 1

Preparation of a mixture of cafestol and kahweol 1000 g of coffee oil containing 11.3% of a mixture of esters of cafestol and kahweol were collected from the spent grounds obtained in the production of instant coffee. To this coffee oil were added 600 ml anhydrous methanol containing 5% by weight of potassium hydroxide and the mixture stirred for 2 hours under nitrogen at ambient temperature. In this step the triglycerides and the esters of cafestol and kahweol are converted to fatty acid methyl esters and alcohols (glycerol, cafestol, kahweol and sterols).

After two hours stirring the reaction mixture was diluted with 1500 ml heptane and then extracted with 1540 ml of aqueous methanol containing 10% water with agitation. The heptanoic phase containing the fatty acid methyl esters was then separated from the aqueous methanol phase which has solubilised the cafestol and kahweol, the glycerol and the potassium hydroxide. The extraction was repeated twice using each time 1500 ml aqueous methanol containing 5% water and the three extracts were combined and concentrated under vacuum to 1200 g. 50 g of potassium hydroxide were dissolved in the concentrated extract and agitated at 40° C. under nitrogen for 30 minutes after which 2 liters of water then added. This solution was then extracted five times with a mixture containing 1800 ml of dichloromethane to which had been added 8% by weight of methanol, and the extract evaporated to dryness to give 64 g of a crude orange-coloured mixture of cafestol and kahweol of 70% purity.

This crude mixture of cafestol and kahweol was then dissolved in 500 ml ethyl acetate and the solution agitated for 1 hour with 30 g of active carbon. The solution was then filtered and evaporated to dryness to give 57 g of an orange-yellow oil was recrystallised in warm methanol to give 50 g of a mixture of cafestol and kahweol containing 40.7% kahweol.

EXAMPLE 2

Preparation of cafestol (a) Formation of the Palladium/calcium carbonate catalyst conditioned by lead.

Palladous chloride (1.48 g, 0.0083 mole) was placed in a 10-ml Erlenmeyer flask, and 3.6 ml (0.043 mole) of 37% hydrochloric acid was added. The flask was shaken at about 30° C. until the palladous chloride had dissolved. The chloropalladous acid solution was transferred to a 150-ml, beaker with 45 ml of distilled water. The beaker was equipped with a pH meter and a magnetic or mechanical stirrer. The pH of the stirred solution was brought to 4.0–4.5 by slow addition of aqueous 3N sodium hydroxide from a buret. A precipitate formed at high local concentrations of sodium hydroxide, but it dissolved on further stirring. The solution was diluted to approximately 100 ml in a graduated cylinder and placed in a 200 ml or 250 ml, three-necked, round-bottomed flask equipped with a mechanical stirrer and a thermometer and partly immersed in a bath of oil or water. Precipitated calcium carbonate (18 g) was added. The well-stirred suspension was heated to 75°–85° C. and held at this temperature until all the palladium had precipitated, as indicated by loss of color from the solution; this took about 15 minutes. With the mixture still at 75°–85° C., 6.0 ml of sodium formate solution (about 0.7N) was added. During the addition, $CO_2$ escaped and the catalyst turned from brown to gray; rapid stirring was essential to keep the mixture from foaming over. An additional 4.5 ml of the sodium formate solution was added, and the reduction was completed by stirring the mixture at 75°–85° C. for 40 minutes. The catalyst, which was then black, was separated on a 10 cm Büchner funnel and washed with eight 65 ml portions of water.

The moist catalyst was placed in a 200 ml or 250 ml round-bottomed flask equipped as described above. Water (60 ml) and 18 ml of a 7.7% solution of commercial grade lead acetate, $Pb(OCOCH_3)_2.3H_2O$, were added. The slurry was stirred and heated at 75°–85° C. for 45 minutes. The catalyst was separated on a 10 cm Büchner funnel, washed with four 50 ml portions of water, sucked as dry as possible, and dried in an oven at 60°–70° C. The dried catalyst, a dark gray powder, weighed 19–19.5 g.

(b) Hydrogenation of the kahweol/cafestol mixture was prepared as in Example 1.

100 g of a mixture of cafestol and kahweol prepared by the method described in Example 1 containing 48.2% cafestol and 40.7% kahweol were dissolved in 2500 ml of 96% ethanol. To this solution were added 21 g of a Palladium/calcium carbonate catalyst prepared as above and 3000 ml of hydrogen were introduced under vigorous stirring over a period of 2 hours 15 minutes. The reaction mixture was then filtered to get rid of the catalyst and concentrated under vacuum to half its volume. 500 ml water was added to the ethanolic solution with stirring to precipitate an insoluble material and the mixture was left to stand overnight at 4° C. before filtering and drying to give 78.2 g of snow-white crystals of cafestol. To the filtrate (1800 ml) were added 250 ml water with stirring to form further insoluble material and the mixture was left for 4 hours at 4° C. before filtering and drying to give a further 10.1 g of snow-white crystals of cafestol. The yield was 88.3 g and the purity of the cafestol was 95%. The cafestol was then recrystallized from methanol to give a yield of 80.0 g and a purity of greater than 99%.

EXAMPLE 3

By carrying out a similar procedure to that described in Example 2b but using a Palladium/active charcoal catalyst conditioned by lead, the yield of cafestol was similar.

COMPARATIVE EXAMPLE A

By carrying out a similar procedure to that described in Example 2b but using a Palladium/barium sulphate catalyst conditioned by lead, all the kahweol was destroyed.

COMPARATIVE EXAMPLE B

By carrying out a similar procedure to that described in Example 2b but using a Palladium-aluminium oxide catalyst conditioned by lead, only 45% of the kahweol was converted to cafestol.

I claim:

1. A process for converting kahweol to cafestol comprising hydrogenating kahweol in the presence of a palladium catalyst which has been partially deactivated by lead and which is on a support selected from the group consisting of a calcium carbonate support and an active carbon support.

2. A process according to claim 1 wherein the amount of catalyst is from 0.1 to 1.0 parts by weight per part by weight of kahweol.

3. A process according to claim 1 wherein the amount of catalyst is from 0.25 and 0.75 parts by weight per part by weight of kahweol.

4. A process according to claim 1 wherein the kahweol is hydrogenated in a solvent selected from the group consisting of an aliphatic alcohol and an aromatic hydrocarbon and after hydrogenation, whereby the cafestol is formed in solution, the catalyst is separated from the solution and the cafestol is precipitated from the solution by addition of water to the solution.

5. A process according to claim 1 further comprising recrystallizing the cafestol from a solvent.

6. A process according to claim 4 further comprising recrystallizing the cafestol from a solvent.

7. A process according to claim 1 wherein the kahweol is present in a mixture comprising cafestol and kahweol.

8. A process according to claim 7 wherein the mixture is derived from coffee oil.

9. A process for converting kahweol to cafestol comprising:
   (a) partially deactivating a palladium catalyst which is on a support selected from the group consisting of a calcium carbonate support and an active carbon support by means of lead; and
   (b) hydrogenating the kahweol in the presence of the partially deactivated catalyst.

10. A process according to claim 9 wherein the source of the lead is lead acetate.

11. A process according to claim 9 wherein the source of the lead is an aqueous solution of lead acetate.

12. A process according to claim 11 further comprising heating the lead acetate solution and the catalyst to partially deactivate the catalyst.

13. A process according to claim 12 further comprising separating the partially deactivated catalyst from the lead acetate solution.

14. A process according to claim 13 wherein the partially deactivated catalyst is separated from the lead acetate solution by filtering.

15. A process according to claim 13 further comprising washing and drying the partially deactivated catalyst after separating it from the lead acetate solution.

16. A process according to claim 9 wherein the kahweol is hydrogenated in a solvent selected from the group consisting of an aliphatic alcohol and an aromatic hydrocarbon.

17. A process according to claim 16 further comprising, after hydrogenating the kahweol and forming the cafestol in solution, separating the partially deactivated catalyst from the solution and precipitating the cafestol from the solution by addition of water.

18. A process according to claim 17 further comprising recrystallizing the cafestol from a solvent.

* * * * *